United States Patent [19]
Nixon et al.

[11] Patent Number: 5,849,600
[45] Date of Patent: Dec. 15, 1998

[54] DIAGNOSTIC ASSAYS FOR ALZHEIMER'S DISEASE

[75] Inventors: Ralph Nixon, Arlington, Mass.; Toshiyuki Honda, Yokohama, Japan

[73] Assignee: The McLean Hospital Corporation, Belmont, Mass.

[21] Appl. No.: 149,975

[22] Filed: Nov. 10, 1993

[51] Int. Cl.$^6$ .................................................. G01N 33/544
[52] U.S. Cl. .......................... 436/518; 436/528; 436/529; 436/530; 436/161; 436/811
[58] Field of Search ..................... 435/7.1, 975; 436/518, 436/530, 547, 524, 528, 529, 811, 161; 530/350, 387.1, 387.9, 389.1

[56] References Cited

FOREIGN PATENT DOCUMENTS 0 391 714   10/1990   European Pat. Off. .
WO 90/15331   12/1990   WIPO .

OTHER PUBLICATIONS

Concha et al., "Rat Annexin V Crystal Structure: Ca$^2$+–Induced Conformational Changes," Science 261:1321–1324, 1993.
Appleyard et al., "Cholinesterase activites in cerebrospinal fluid of patients with senile dementia of Alzheimer type", Brain 110:1309–1322 (1987).
Barton et al., "Amino acid sequence analysis of the annexin super–gene family of proteins", Eur. J. Biochem. 198:749–760 (1991).
Braselmann et al., "Identification of Fos target genes by the use of selective induction", J. Cell Science Supp. 16:97–109 (1992).
Creutz, "The Annexins and Exocytosis", Science 258:924–930, 1992.
Crompton et al., "Diversity in the Lipocortin/Calpactin Family", Cell 55:1–3, 1988.
Davidson et al., "Binding and inhibition stidues on lipocortins using phosphatidylcholine vesicles and phospholipase A$_2$ from snake venom, pancreas, and a macrophage–like cell line" J Bio Chem 265:5602–560, 1990.
Donato et al., "Two novel brain proteins, CaBP33 and CaBP37, are calcium–dependent phospholipid–and membrane–binding proteins", FEBS LTRS 262:72–76, 1990.
Erikson et al., "Identification of a cellular protein substrate phosphorylated by the Avian Sarcoma Virus–transforming gene product", Cell 21:829–836, 1980.
Glenner et al., "Alzheimer's disease: initial report of the purification and characterization of a novel cerebrovascular amyloid protein", BBRC 120:885–890, 1984.
Huber et al., "The crystal and molecular structure of human annexin V, an anticoagulant protein that binds to calcium and membranes", EMBO J. 9:3867–3874, 1990.
Kang et al., "The precursor of Alzheimer's disease amyloid A4 protein resembles a cell–surface receptor", Nature 325:733–736, 1987.
Karshikov et al., "Annixin V membrane interaction: an electrostatic potential study", Eur Biophys J 20:337–344, 1992.

Laemmli, "Cleavage of structural proteins during the assembly of the head of bacteriophage T4" Nature 227:680–685, 1970.
Learmonth et al., "Novel isoforms of CaBP 33/37 (Annexin V) from mammalian brain: structural and phosphorylation differences that suggest distinct biological roles", Biochimica et Biophysica Acta 1160:76–83, 1992.
Mangeat, "Interaction of biological membranes with the cytoskeletal framework of living cells", Biology of the Cell 64:261–281, 1988.
Marotta et al., "Overexpression of amyloid precursor protein A4 (Beta–amyloid) immunoreactivity in genetically transformed cells: Implications for a cellular model of Alzheimer amyloidosis", PNAS 86:337–341, 1989.
Pollard et al., "Ca$^{2+}$–activated synexin forms highly selective, voltage–gated Ca$^{2+}$channels in phosphatidyl–serine bilayer membranes", PNAS USA 85:2974–2978, 1988.
Pula et al., Characterization of mammalian heart annexins with special reference to CaBP33 (annexin V) FEBS 277:53–58, 1990.
Rojas et al., "Calcium–activate Endonexin II forms calcium channels across acidic phospholipid bilayer membranes", J Bio Chem 265:21207–21215, 1990.
Roth et al., "Correclation between scores for dementia and counts of 'senile plaques' in cerebral grey matter of elderly subjects", Nature 209:109–110, 1966.
Schagger et al., "Tricine–sodium dodecyl sulfate–polyacrylamide gel electrophoresis for the separation of proteins in the range from 1 to 100 kDa", Analy Biochem 166:367–379, 1987.
Schlaepfer et al., "Expression annexins as a function of cellular growth state", J Cell Biology 111:229–238, 1990.
Tait et al., "Placental anticoagulant proteins: isolation and comparative characterization of four members of the lipocortin family", Biochemistry 27:6268–6276, 1988.
Seubert et al., "Isolation and quantification of soluble Alzheimer's beta–peptide from biological fluids", Nature 359:325–327, 1992.
Towbin et al., "Electrophoretic transfer of proteins from polyacrylamide gels to nitrocellulose sheets: procedure and some applications", PNAS USA 76:4350–4354, 1979.
Takeuchi et al., "Immunoassay and activity of calcium–activated neutral proteinase (mCANP): distribution in soluble and membrane–associated fractions in human and mouse brain", J Neurochem 58:1526–1532, 1992.

(List continued on next page.)

*Primary Examiner*—Patricia Duffy
*Attorney, Agent, or Firm*—Clark & Elbing LLP

[57] ABSTRACT

The invention provides a method of diagnosing Alzheimer's disease in a human patient by measuring the amount of p33 present in a biological sample from a patient who may have Alzheimer's disease relative to the amount of p33 in a control sample from an unaffected human. Also included in the invention are diagnostic kits for Alzheimer's disease and methods of screening for effective therapeutics for Alzheimer's disease.

5 Claims, 13 Drawing Sheets

OTHER PUBLICATIONS

Wester et al., "Ventricular cerebrospinal fluid monoamine transmitter and metabolite concentrations reflect human brain neurochemistry in autopsy cases", J Neurochem 54:1148–1156, 1990.

Wisniewski et al., "Reexamination of the pathogensis of the senile plaque", Progress in Neuropathology pp. 1–25.

Zain et al., "Molecular cloning of amyloid cDNA derived from mRNA of the Alzheimer disease brain: coding and noncoding regions of the fetal precursor mRNA are expressed in the cortex", PNAS USA 85:929–933, 1988.

Henricksson et al, J. Neurochem, Mar. 1991, vol. 56, No. 3, pp. 1037–1042; "Analysis and quantitation of the β–amyloid precursor . . . ".

Campbell, AM. "Monoclonal Antibody and Immuno Sensor Technology In: Laboratory Techniques in Biochemistry and Molecular Biology" 1991, VL6t ed Elsevier, Amsterdam pp. 1–4.

Tham et al, J. Neural. Transm. Park Dis. Demont. Sec. (Austria) vol. 5 No. 3. pp. 165–176 1993, "Insulin–like Growth Factor . . . ".

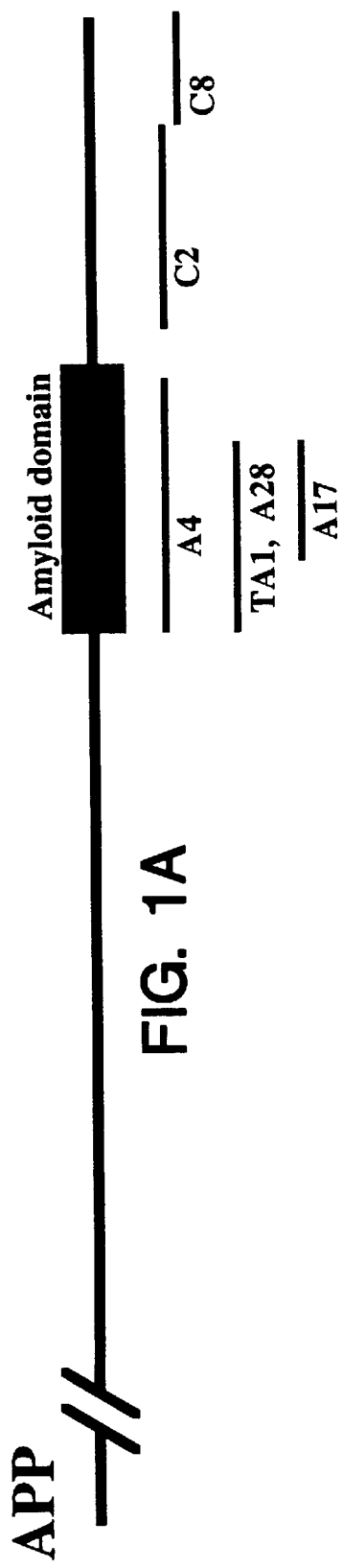
FIG. 1A
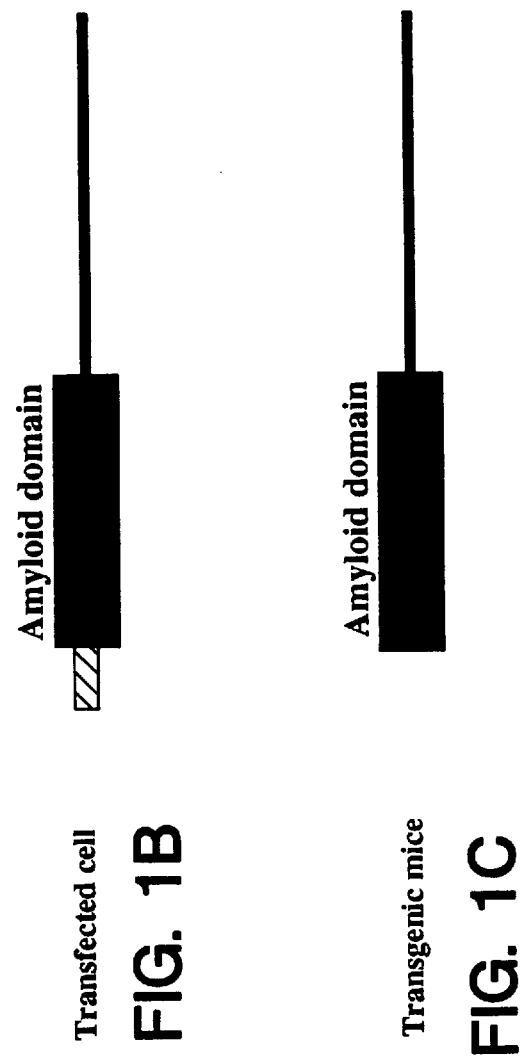
FIG. 1B Transfected cell
FIG. 1C Transgenic mice

A4-C

A4-C

PC12

PC12

```
              10          20          30          40          50
MALRGTVTDF  SGFDGRADAE  VLRKAMKGLG  TDEDSILNLL  TARSNAQRQQ
IAEEFKTLFG  RDLVNDMKSE  LTGKFEKLIV  ALMKPSRLYD  AYELKHALKG
AGTDEKVLTE  IIASRTPEEL  RAIKQAYEEE  YGSNLEDDVV  GDTSGYYQRM
LVVLLQANRD  PDTAIDDAQV  ELDAQALFQA  GELKWGTDEE  KFITILGTRS
VSHLRRVFDK  YMTISGFQIE  ETIDRETSGN  LENLLLAVVK  SIRSIPAYLA
ETLYYAMKGA  GTDDHTLIRV  IVSRSEIDLF  NIRKEFRKNF  ATSLYSMIKG
DTSGDYKKAL  LLLCGGEDD
```

FIG. 9

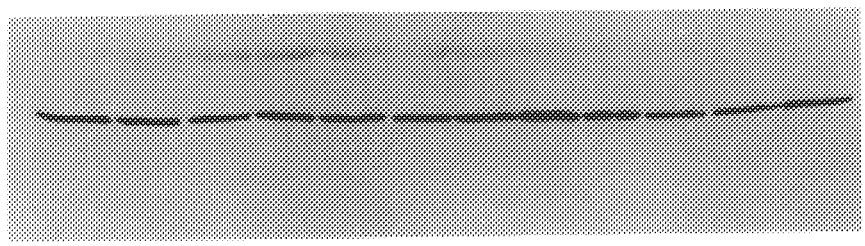
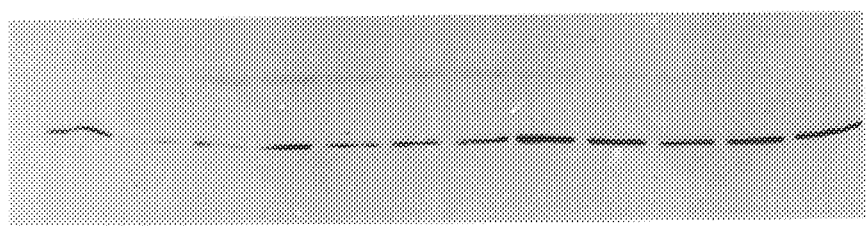
FIG. 11A

DIAGNOSTIC ASSAYS FOR ALZHEIMER'S DISEASE

This invention was made with Government support under Contract #AG 08278 and AG 10916 awarded by the National Institutes of Health. The Government has certain rights in this invention.

BACKGROUND OF THE INVENTION

This invention relates to diagnosis of Alzheimer's disease.

Alzheimer's disease (AD) is a devastating impairment of cognitive function prevalent in individuals generally forty-five or older. Despite the toll taken by this disease, it remains poorly understood. The degree of dementia in AD has been correlated with the number of senile plaques (SPs) found in the cerebral cortex of AD patients (Roth et al., Nature 209:109, 1966). Histologically, SPs are surrounded by degenerating neurites and reactive astrocytes (Wisniewski and Terry, Progress in Neuropathology 2:23, 1973), and biochemically, SPs contain a small insoluble fibrillary protein termed β-amyloid (Glenner and Wong, Biochem. Biophys. Res. Commun. 120:885–890). Molecular cloning of the β-amyloid gene from normal fetal tissue (Kang et al., Nature 325:733–736, 1987) and AD brain tissue (Zain et al., Proc. Natl. Acad. Sci. USA 85:929–933, 1988) has revealed that it is derived from a larger precursor protein, the amyloid precursor protein (APP). In addition to senile plaques, Alzheimer's disease is characterized by abundant neurofibrillary tangles in neuronal perikarya and proximal dendrites, and granulovacuolar degeneration in pyramidal cells of the hippocampus.

The cause of AD is not known, nor is there a treatment for AD. In addition, there is no diagnostic test for AD in either pre-symptomatic or symptomatic patients. Current methods used to diagnose AD involve analysis of cerebrospinal fluid (CSF) or brain tissue obtained from postmortem patients.

The annexins (or lipocortins) are a family of proteins which bind to negatively charged phospholipids in a calcium-dependent manner. They are found in a variety of cell types in higher and lower eukaryotes. The annexin family of calcium binding proteins shows features of both soluble and membrane proteins. The primary sequences of the 13 known annexin family members are largely composed of four highly conserved homologous repeats. In contrast to the bulk of the protein, the N termini of the annexins differ greatly in length and sequence (Crompton et al., Cell 55:1–3, 1988; Barton et al., Eur. J. Biochem. 198:749–760, 1991).

The in vivo role of the annexins is unknown. One proposed function is involvement in membrane-membrane fusion and exocytosis (Creutz, Science 258:924–931, 1992). In addition, roles for annexins have been proposed involving interactions with cytoskeletal proteins (Mangeat, Biol. Cell. 64:261–281), anticoagulant activities (Tait et al., Biochemistry 27:6268–6276), inhibition of phospholipase $A_2$ in the regulation of inflammation (Davidson et al., J. Biol. Chem. 265:5602–5609, 1990), and the formation of calcium selective ion channels in phospholipid bilayers by annexin V and VII (Pollard et al., Proc. Natl. Acad. Sci. USA 85:2974–2978, 1988; Rojas et al., J. Biol. Chem. 265:21207–21215, 1990; Karshikov et al., Eur. Biophys. J. 20:337–344, 1992). Some members of the annexin family are expressed in a growth-dependent manner (Schlaepfer and Haigler, J. Cell. Biol. 111:229–238, 1990) and are targets for cellular kinases in vivo (Moss et al., Novel Calcium Binding Proteins (Claus W. Heizmann, Ed.) Springer, Berlin, 1991; Erikson and Erikson, Cell 21:829–836, 1980).

SUMMARY OF THE INVENTION

We have shown that a 33 kD protein (p33) is specifically enriched in CSF and brain homogenates from Alzheimer's patients relative to controls. Thus, detection and quantification of the 33 kD protein is useful for diagnosing Alzheimer's disease.

Accordingly, in the first aspect, the invention provides a method for diagnosing Alzheimer's disease in a human patient. In this method, the amount of p33 present in a biological sample from a patient is determined relative to the amount of p33 present in a control sample of the same type (e.g., lumbar or ventricular CSF, brain homogenate, or cortex thin section) from an unaffected human. A relative level of p33 in the sample from the patient which is 50 percent above the level in the control sample, or more preferably 150 percent, or most preferably 300 percent, indicates a diagnosis of Alzheimer's disease.

Measurement of p33 levels is achieved by the use of an immunoassay which allows detection of binding between p33 and an antibody. The amount of binding can be determined by analysis of enzymatic, chromodynamic, radioactive, or luminescent labels that are attached to either the antibody which binds p33 or to a secondary antibody which recognizes the antibody which binds to p33. Immunoassays which may be used include, but are not limited to, ELISA, inhibition ELISA, Western blots, immunoprecipitation, slot or dot blot assays, immunostaining, RIA, fluorescent immunoassays using antibody conjugates or antigen conjugates of fluorescent substances such as fluorescein or rhodamine, Ouchterlony double diffusion analysis, and immunoassays employing an avidin-biotin or streptavidin-biotin detection system.

These methods allow detection of p33 present in biological samples which, for the purpose of Alzheimer's diagnosis, may include, but are not limited to, lumbar CSF, ventricular CSF, brain tissue homogenates, or thin sections obtained from the patient. Analysis of lumbar CSF is particularly useful, as it may be performed using samples obtained from a living patient. Previously, no diagnostic for detecting AD in living patients has been available.

The antibodies useful for the methods of the invention include those which are substantially specific in their binding of p33, annexin V, or the C2 fragment of APP; specifically, the antibodies 4431 or TC2 may be used in the methods and preparations of the invention. It is understood that some of the antibodies of the invention may recognize proteins in addition to p33. In the cases of such antibodies, immunoassays that allow differentiation of protein size and weight are most useful.

The invention also includes substantially pure preparations of p33 and fragments thereof, and substantially pure C2 peptide (amino acids 644–676 of APP) (SEQ ID NO:5). These proteins (p33 and fragments thereof and the C2 peptide) have many utilities. For example, they can be used in methods for screening for compounds which are useful therapeutic agents for AD. In addition, they can be used as control standards in the diagnostic methods and kits of the invention.

In the second aspect, the invention provides a method of producing an antibody which specifically recognizes p33. This method involves immunizing a mammal with substantially pure p33, annexin V or an immunogenic fragment thereof, or the C2 fragment of APP (conjugated to a carrier, if necessary). Polyclonal antisera can then be isolated from the immunized mammal and purified. Alternatively, an antibody-producing organ from the immunized animal can be harvested and a cellular homogenate prepared from the organ can be fused to cultured cancer cells. Hybrid cells which produce monoclonal antibodies specific for p33 can be selected.

The third aspect of the invention provides a kit for in vitro diagnosis of Alzheimer's disease by detection of p33 in a biological sample from a patient. A kit for detecting p33 may include (1) a primary antibody capable of binding to p33; and (2) a secondary antibody conjugated to a signal-producing label, the secondary antibody being capable of binding to p33, but to a site different from (i.e., spaced from) that to which the first monoclonal antibody binds. Such antibodies can be prepared by methods well known in the art. This kit is most suitable for carrying out a two-antibody sandwich immunoassay, e.g., two-antibody sandwich ELISA.

Another kit which is useful for detection of p33 and a part of the invention includes: (1) a primary antibody capable of binding to p33; and (2) a secondary antibody conjugated to a signal-producing label, the secondary antibody being capable of binding to the primary antibody.

In each of the above-described assay kits, the signal-producing label linked to the secondary antibody may be, but is not limited to, an enzyme (e.g., horseradish peroxidase or alkaline phosphatase). Preferably, both the enzyme and its substrate are provided in the kit. An uncoated support can also be included in the kit onto which the first antibody (in the first kit described above) or the sample to be assayed (in the second kit described above) can be immobilized by the user. The kit may also include a purified protein, e.g., p33, to be used as a standard.

The fourth aspect of the invention features a method of decreasing the level of p33 in brain tissue by introducing into the patient, most preferably into the brain tissue, a compound which decreases the level of p33. Such compounds identified by using this method can be used to treat patients who are presymptomatic or symptomatic for Alzheimer's disease.

The fifth aspect of the invention features a method for measuring the ability of a candidate compound to decrease the level of p33. In this method, a cell that expresses p33 is contacted with a candidate compound and the level of p33 in the cell is determined. This determination of p33 levels may be made using any of the above-described immunoassays. The cell can be an A4-C transfected PC12 or, alternatively, a fibroblast taken from a skin biopsy from a patient, or any other p33 expressing cell type.

The invention features another method for measuring the ability of a candidate compound to decrease the level of p33. In this method, a candidate compound is administered to a mammal that expresses p33. The mammal can be a mouse that expresses an A4-C transgene (Sandhu et al., Journal of Biological Chemistry 266:21331, 1991). The level of p33 can be determined by analysis of a tissue sample, e.g., a brain homogenate or cortex thin section, from the mouse using the immunoassays described above.

As used herein, the term "substantially pure" describes a compound, e.g., a protein or polypeptide, e.g., a p33 protein or fragment thereof, or a C2 peptide of APP, which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99%, of the total material (by volume, by wet or dry weight, or by mole percent or mole fraction) in a sample is the compound of interest. Purity can be measured by any appropriate method, e.g., in the case of polypeptides by column chromatography, polyacrylamide gel electrophoresis, or HPLC analysis. A compound, e.g., a protein, is also substantially purified when it is essentially free of naturally associated components or when it is separated from the native contaminants which accompany it in its natural state.

The term "specifically binding", with reference to the antibodies of the invention, refers to the interaction of an antibody and an antigen (e.g., the interaction of TC2 or 4431 with p33, annexin V, or the C2 fragment of APP). When an antibody has an affinity constant (kD) of at most $10^{-7}$ moles/liter or preferably, $10^{-8}$ moles/liter, for an antigen, it is said to be capable of specific binding (alternatively referred to as "contacting" or "binding") to that antigen. On the other hand, when an antibody has a kD value of at least $10^{-2}$ moles/liter or higher for an antigen, it is said to be incapable of binding to that antigen. The antibodies defined herein can be either monoclonal or polyclonal.

An advantageous feature of the invention is that it provides a diagnostic assay for AD in a patient who is either symptomatic or asymptomatic. Patients most likely to benefit from the diagnostic assays of the invention are those that present with early symptoms of Alzheimer's disease, such as changes in personality, difficulty with word finding, memory loss, particularly loss of recent memories, misplacement objects, forgetting names, and progressive loss of word fluency. This diagnosis allows intervention and, possibly, the administration of therapeutic remedies for affected individuals. In addition, this diagnosis allows the physician to make a distinction between AD and other diseases that are characterized by similar symptoms. Analysis of lumbar CSF is a low risk assay which is a suitable diagnostic method for living patients. The CSF may be withdrawn on an outpatient basis and results obtained within a matter of hours or days. In addition, the invention provides an easy and reliable method for postmortem diagnosis of AD.

Other features and advantages of the invention will become apparent from the following detailed description, the drawings, and from the claims.

DETAILED DESCRIPTION

The drawings are first described.

Drawings

FIGS. 1A–1C are a schematic representation of APP and A4-C peptides. In addition, peptides within APP to which antibodies have been raised are indicated.

Figure 2A:
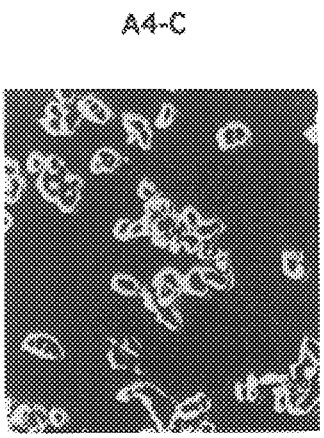
FIGS. 2A–2D are phase contrast micrographs of transfected PC12 cells expressing A4-C (panels 2A and 2B) and control PC12 cells (panels 2C and 2D) that were cultured for 7 days in the absence (panels 2A and 2C) or presence (panels 2B and 2D) of 50 ng/ml NGF.
Figure 2B:
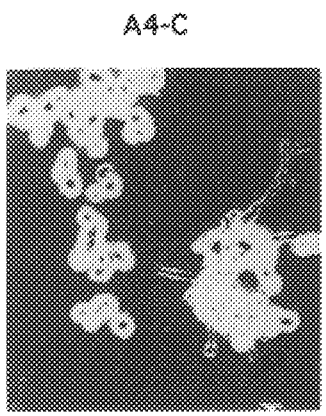
Figure 2C:
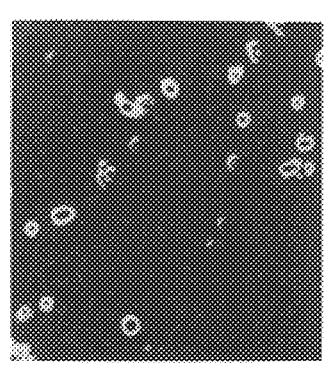
Figure 2D:
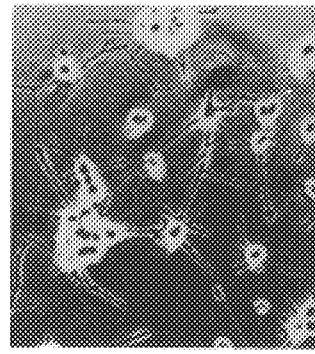
Figure 3A:
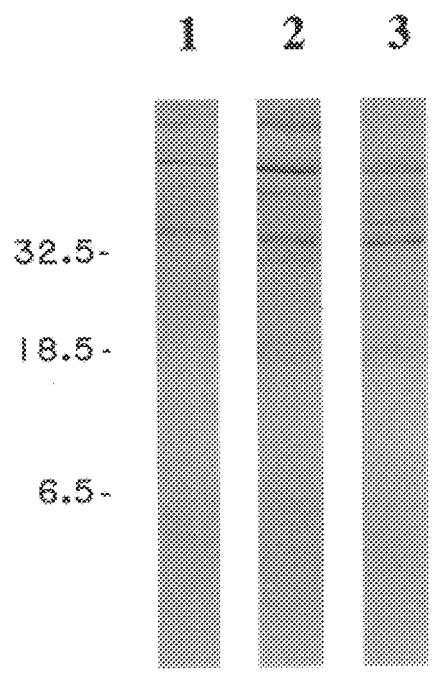
Figure 3B:
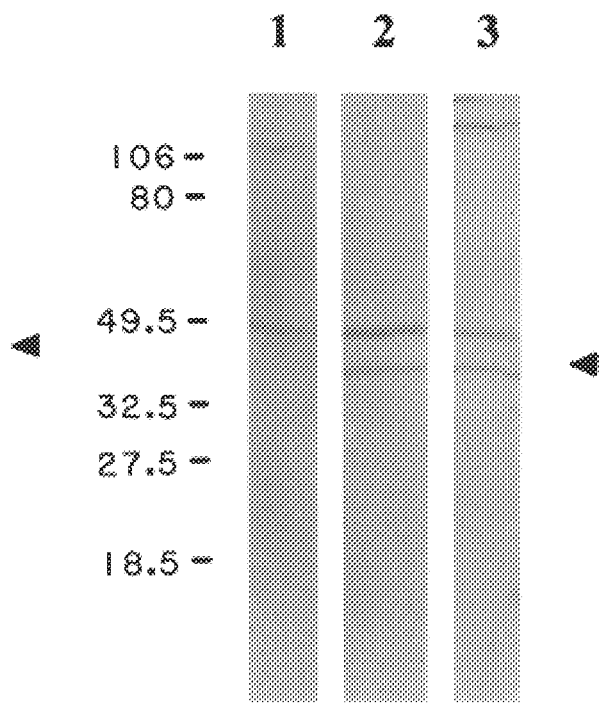

FIGS. 3A–3B are an immunoblot of lysates from control PC12 cells (lane 1) and PC12 cells expressing A4-C (lanes 2 and 3) probed with A4 (panel 3A) or TC2 (panel 3B) antibodies.

Figure 4:
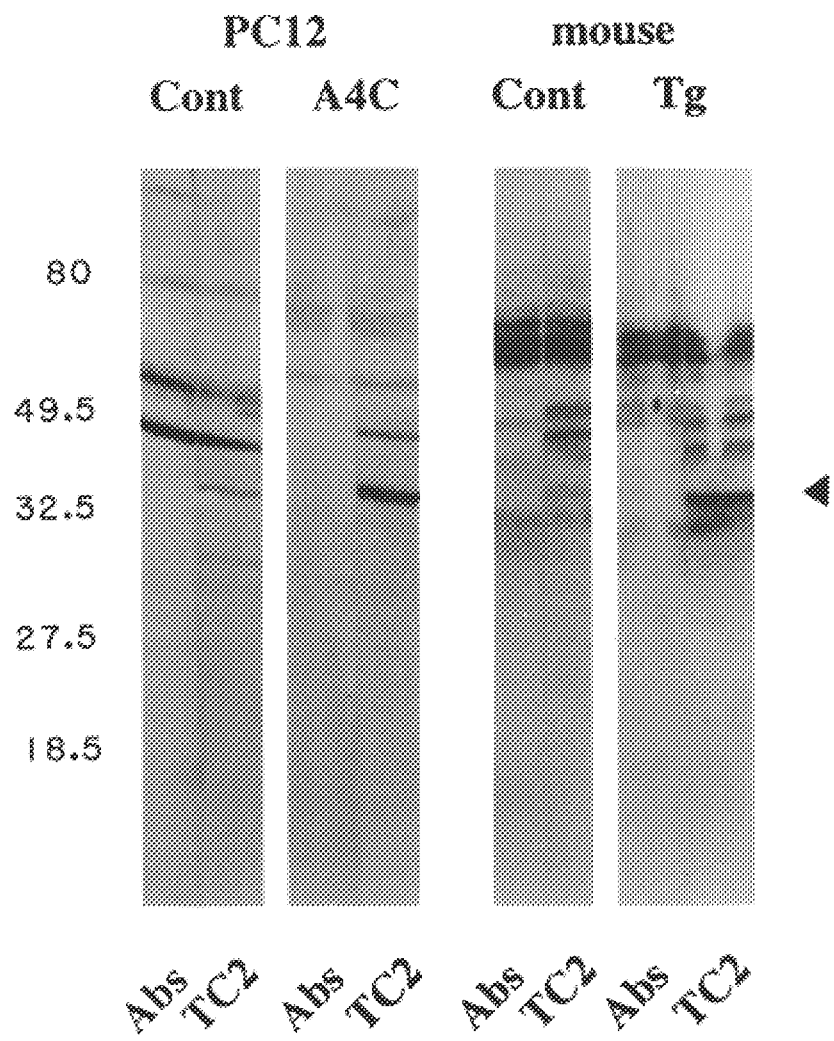

FIG. 4 is an immunoblot of A4-C transfected and control PC12 lysates and A4-C transgenic and control mouse brain homogenates probed with TC2.

Figure 5:
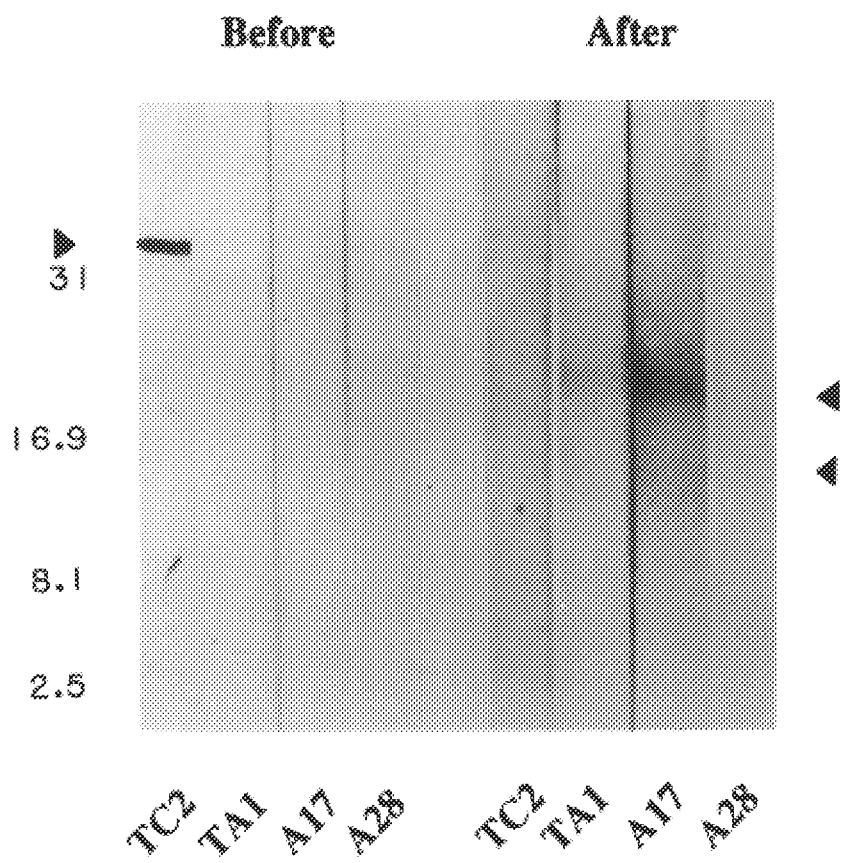

FIG. 5 is an immunoblot of purified 33 kD protein before and after CNBr cleavage. The blot was probed with the indicated antibodies.

Figure 6:
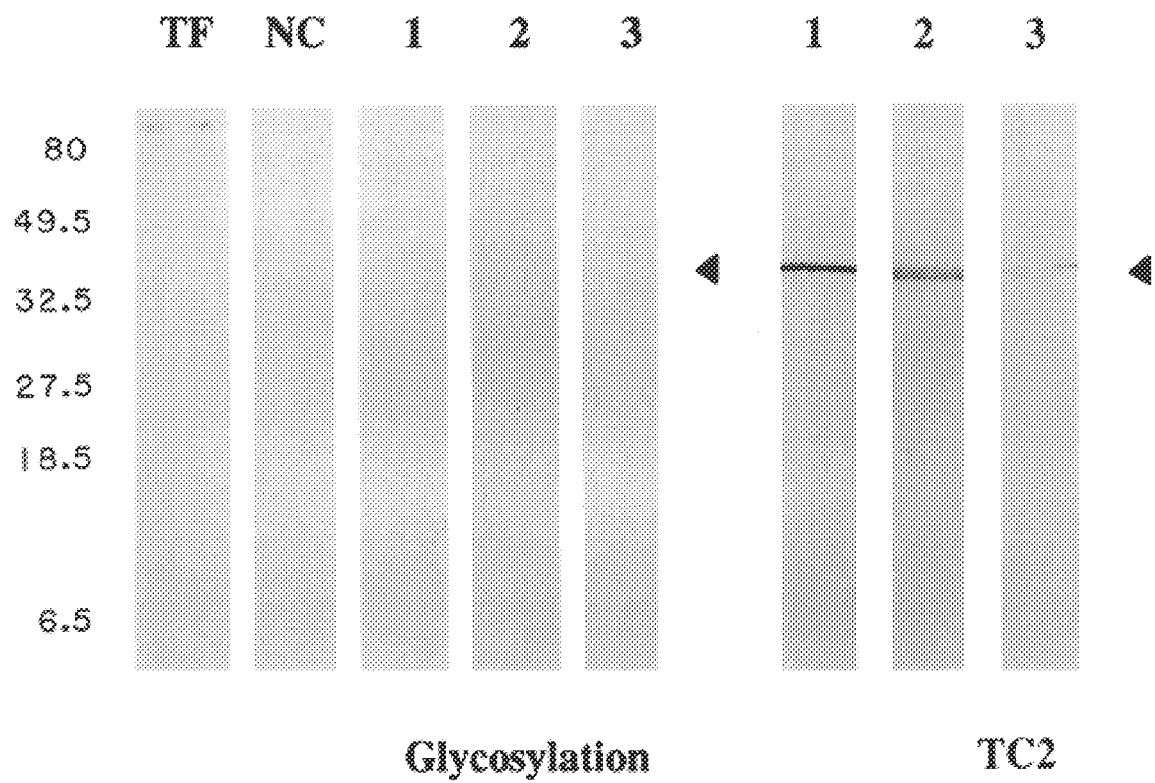

FIG. 6 is an analysis of the glycosylation state of the 33 kD protein.

Figure 7:
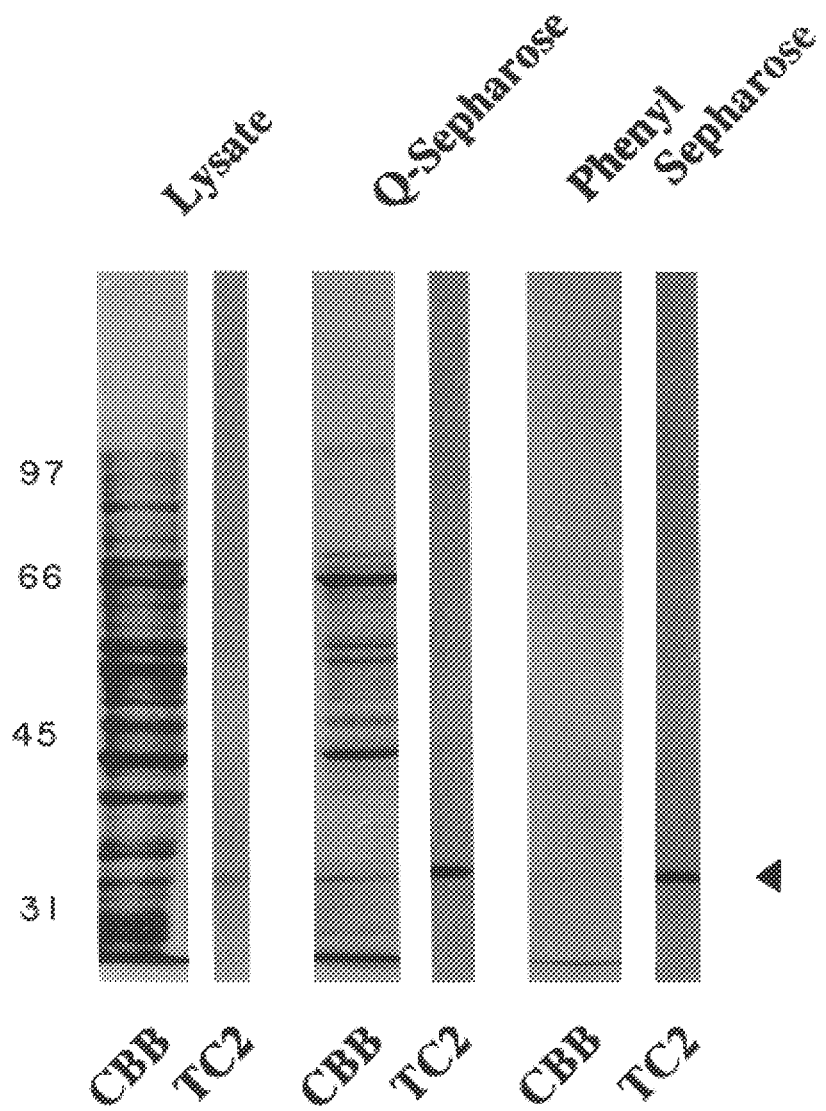

FIG. 7 is Coomassie staining and immunoblot analysis (TC2 probe) showing the purification of the 33 kD protein.

Figure 8:
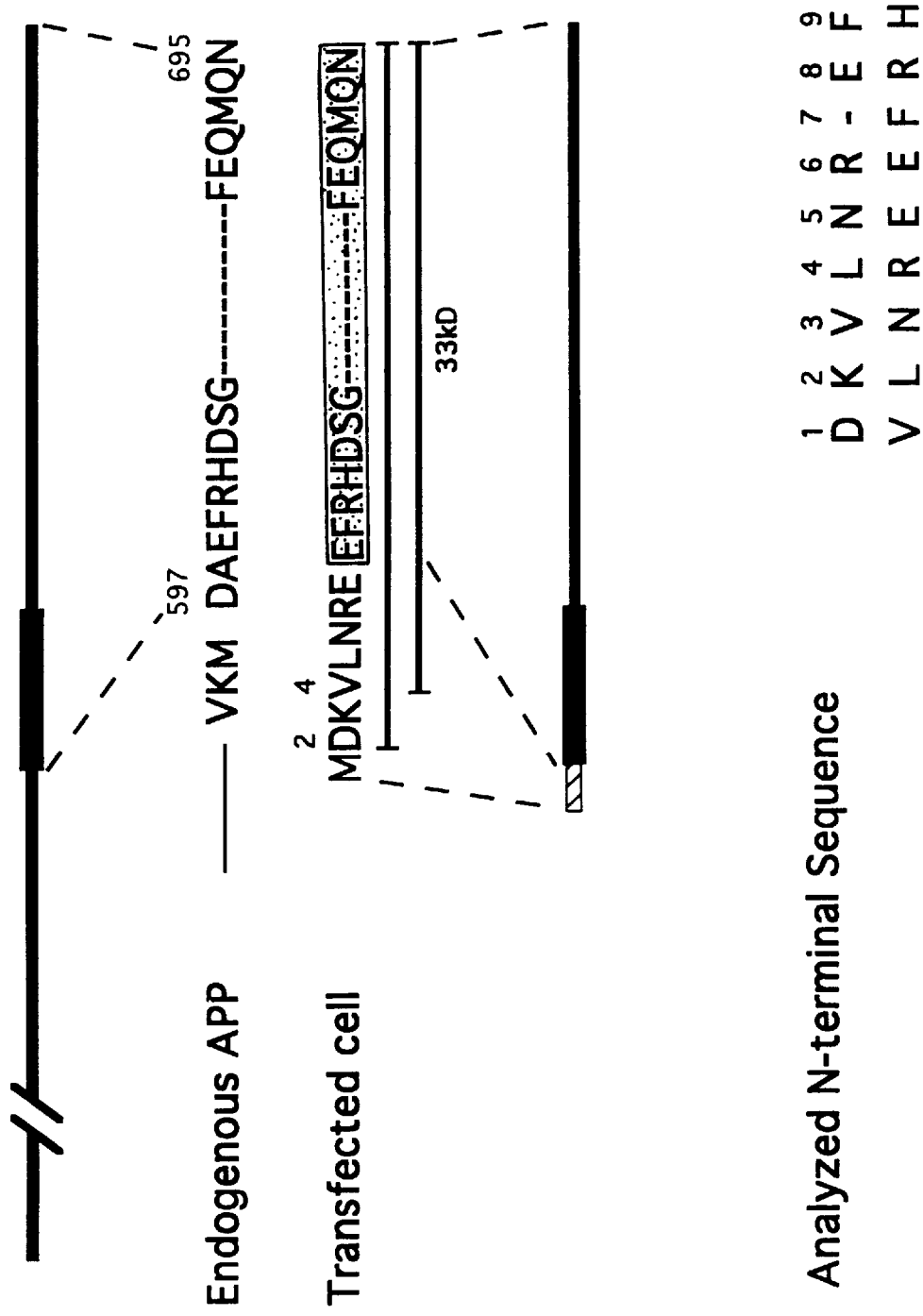

FIG. 8 is a schematic representation of N-terminal sequence analysis of the 33 kD protein purified from transfected cell lysates (SEQ ID NO: 1); Endogenenous APP (SEQ ID NO:3); and the transfected cell (SEQ ID NO: 4).

FIG. 9 shows the sequence of rat annexin V. Peptides sequenced from lysyl endopeptidase cleaved 33 kD protein are underlined and in bold (SEQ ID NO: 2).

Figure 10:
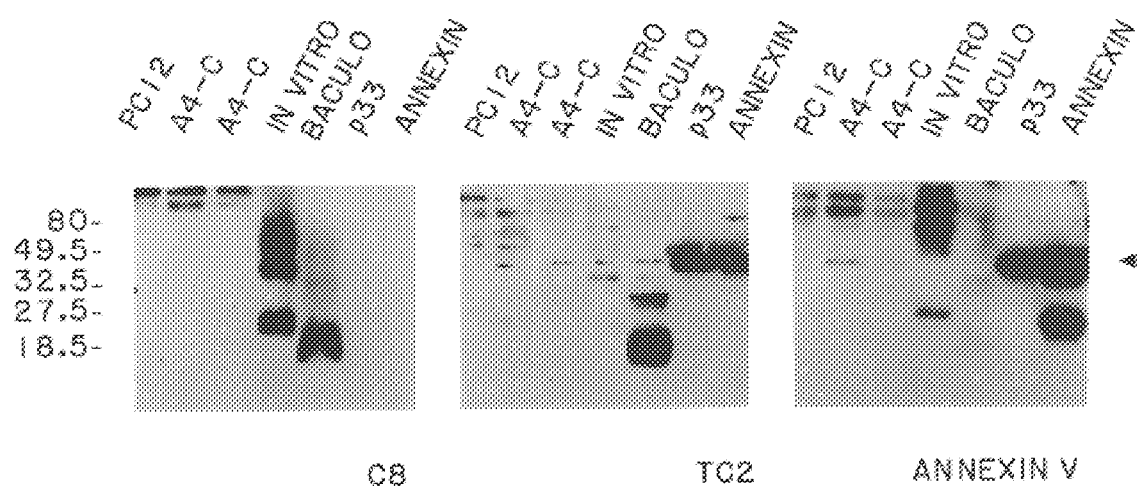

FIG. 10 is immunoblots of control and A4-C transfected PC12 cell lysates, in vitro translated A4-C, baculovirus-produced A4-C, purified 33 kD protein, and purified annexin V. The blots were probed with C8, TC2, and annexin V antibodies.

Figure 11B:
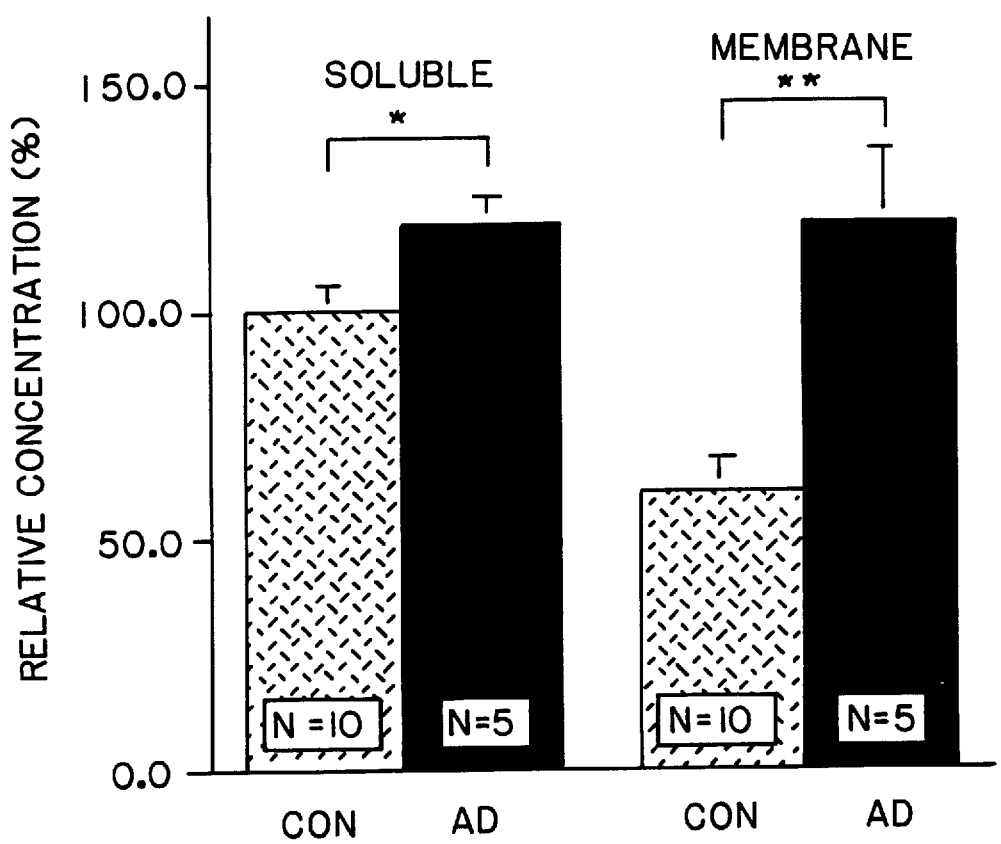

FIG. 11A is an immunoblot of soluble and membrane fractions of homogenates from control and AD human brains. The blot was probed with TC2. FIG. 11B is a schematic representation of quantification of the 33 kD protein detected in 8A.

Figure 12:
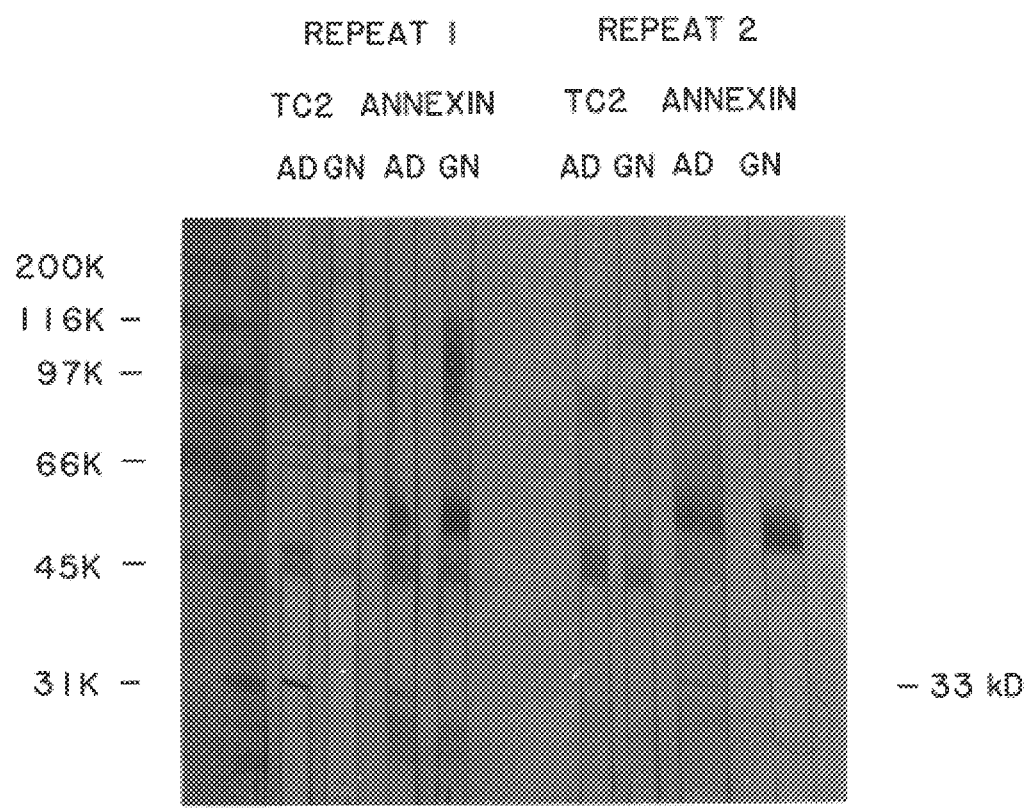

FIG. 12 is immunoblots of ventricular CSF probed with TC2 and an antibody to annexin V (4431).

I. Characterization of p33

PC12 cells overexpressing the A4-C fragment (the C-terminal 100 residues of APP; FIG. 1) under control of the SV40 promoter were constructed. The A4-C fragment has been previously implicated in AD due to an observed neurotoxicity caused by the fragment in cell culture (Yanker et al., Science 245:417, 1989). Using these cell lines we have found that expression of A4-C results in the appearance of a novel 33 kD protein, designated p33. This protein is uniquely over-expressed in AD patients (see below).

Two independent G418-resistant clonal cell lines, designated F100 and G100, were isolated. These cell lines demonstrated stronger immunostaining with antibodies that recognize the amyloid region of APP (antibodies A28 and A17, see FIG. 1) relative to control PC12 cells (Cells were fixed with 4% paraformaldehyde containing 4% sucrose, 0.25% glutaraldehyde in PBS for 15 minutes and rinsed with PBS 2 times for 1 minute. Fixed cells were permeabilized with 0.25% Triton X-100, in PBS for 5 minutes. After blocking with 20% normal goat serum for 15 minutes, cells were incubated with primary antibodies in 2% normal goat serum in PBS overnight at 4° C. Horseradish peroxidase conjugated secondary antibodies were used and DAB was used as a chromagen).

The A4-C fragment has been reported to be toxic to neuronal cells (Yanker et al., Science 245:417, 1989; Kozlowski et al., Journal of Neuroscience 12:1679, 1992). Thus, the effects of A4-C expression in PC12 cells cultured in the presence and absence of nerve growth factor (NGF) was investigated (FIG. 2). PC12 cells transfected with A4-C were larger than control cells and tended to clump together (FIG. 2, compare panels A and C). When control cells were cultured in the presence of NGF, they were observed to differentiate and extend neurites, as expected (FIG. 2, panel D). In contrast, most of the A4-C transfected cells did not respond to NGF and continued to grow steadily (FIG. 2, panel B). No obvious difference in cell number was observed between A4-C transfected cells treated with and without NGF (FIG. 2, compare panels A and B). Thus, our observations indicate that expression of A4-C blocks NGF-induced neuronal differentiation in PC12 cells.

To further characterize A4-C expression in PC12 cells, Western blot analysis of lysates prepared from F100 and G100 cell lines and control PC12 cells was carried out. The predicted molecular weight of the protein encoded by A4-C is 16 kD. Thus, not surprisingly, an anti-amyloid antibody (Boehringer Mannheim) recognized a 16 kD protein in lysates of A4-C transfected PC12 cells, but not in control lysates (FIG. 3, panel A). In contrast, TC2 antibody, which was raised against a synthetic peptide containing the C2 region of APP (FIG. 1; amino acids 644–676(SEQ ID NO:5) ; See Example I, below), recognized a 33 kD protein in A4-C lysates, but not in control lysates (FIG. 3, panel B). In addition, TC-2 recognized a 33 kD protein in brain homogenates from mice transgenic for A4-C, but not in control homogenates (FIG. 4). Staining of the 33 kD protein in lysates from A4-C transfected cells and brain homogenates from A4-C transgenic mice was C2 specific, as the TC2 antibody had been affinity purified and staining of the 33 kD protein was diminished when the antibody was preabsorbed with C2 peptide (FIG. 4). Western analysis of cyanogen bromide-cleaved 33 kD protein using anti-amyloid antibodies revealed that the 33 kD protein contains an amyloid region other than the C2 epitope (FIG. 5; Cyanogen Bromide cleavage was carried out as follows. After electrophoresis, the 33 kD band was cut out of the gel and the gel slice was lyophilized. The dried gel was incubated with CNBr in 70% (v/v) formic acid at 37° C. for 16 hours at a protein/CNBr molecule ratio of 1:20–100. After the reaction, the gel was lyophilized again and incubated with 0.1 M $NH_2HCO_3$ for 5 hours at 37° C. After lyophilization, the dried gel was incubated with Laemmli sample buffer and subjected to Western blot analysis).

The observation that TC2 recognized a 33 kD protein, rather than a protein of the predicted size of 16 kD for A4-C, indicated that 1) TC2 may be detecting an aggregate of A4-C; 2) that A4-C is post-translationally modified; or 3) that TC2 may be crossreactive with a 33 kD protein that is otherwise unrelated to A4-C.

To determine whether the 16 kD A4-C protein abnormally aggregates to form the 33 kD protein, formic acid and urea were used to dissociate the putative aggregates. The 33 kD protein was incubated in 90% formic acid for 24 hours at room temperature. After formic acid treatment, the sample was lyophilized and fractionated by SDS-PAGE. No change in mobility of the 33 kD protein was observed. Similarly, pretreatment of the 33 kD protein with 8M urea and fractionation of the protein by SDS-PAGE in the presence of 6M urea did not result in a change in mobility of the 33 kD protein. Experiments directed at determining whether A4-C is post-translationally modified revealed that it is neither glycosylated (FIG. 6; DIG Glycan Detection Kit was purchased from Boehringer Mannheim and detection was carried out by manufacturer's instructions) nor ubiquitinated.

II. The 33 kD protein contains Annexin V

Further characterization of the 33 kD protein was achieved by protein purification and peptide sequence analysis. The 33 kD protein was purified from lysates of A4-C transfected PC12 (PC12 cells are available from the American Type Culture Collection, Rockville, Md., ATCC# CRL 1721) cells by employing a series of standard chromatographic methods. Briefly, the supernatant from lysates of A4-C transfected PC12 cells was applied to a Q-Sepharose column (3 ml, equilibrated in 50 mM Tris, (pH 7.4)). Proteins bound to the Q-Sepharose column were eluted in 200 mM NaCl and the NaCl concentration in the sample was raised to 1.5M before being applied to a Phenyl-Sepharose column (3 ml, equilibrated in 50 mM Tris (pH 7.4), 1.5M NaCl). Bound proteins were eluted from the Phenyl-Sepharose column in 50 mM Tris (pH 7.4), dialyzed against 50 mM Tris (pH 7.4), and applied to a Mono-Q column (0.5×5 cm) from which protein was eluted with a linear gradient of 125–250 mM NaCl at a flow rate of 0.75 ml/minute over 20 minutes. FIG. 7 shows Coomassie staining and Western blot analysis (TC2 antibody) of samples from along the purification pathway fractionated by SDS-PAGE.

N-terminal sequence analysis of the purified 33 kD protein revealed that it is encoded by the A4-C transgene, and does not correspond to endogenous APP (FIG. 8; Pooled Mono-Q fractions containing the 33 kD protein was separated by 10% Laemmli SDS-PAGE and electrotransferred onto a PVDF (Millipore or Bio-Rad) membrane. After staining with Coomassie Brilliant Blue, automated Edman degradation of the blotted protein was performed on Applied Biosystems Model 470A sequencer. The assignment of PTH amino acids was performed by reverse phase HPLC). This analysis also revealed that the 33 kD protein contains multiple distinct peptides. Thus, further sequence analysis was carried out in order to identify the additional components of the 33 kD protein (FIG. 9). After lysyl endopeptidase digestion of purified 33 kD protein, peptides were separated by reverse phase HPLC, and four of the peptides were sequenced by standard methods, as described above. The sequences of these peptides completely matched internal sequences of annexin V (FIG. 9; 57–68, 85–95, 107–120 and 259–284). Additional support for the presence of annexin V in the 33 kD protein was provided by the observation that an antibody raised to annexin V (herein referred to as "4431") recognized the 33 kD protein in Western blot analysis (FIG. 10). In addition, Western blot analysis revealed that TC2 antibody raised against the C2 fragment of APP recognized purified annexin V (FIG. 10).

The observation that detection of the 33 kD protein depends upon expression of A4-C coupled with the fact that A4-C is a fragment of APP which is associated with the senile plaques characteristic of Alzheimer's disease, indicate that detection of the 33 kD protein may be useful for diagnosing AD. Thus, we examined the usefulness of detection of the 33 kD protein by utilizing antibodies that recognize the 33 kD protein (such as those to annexin V and the C2 region of APP), as described in detail below.

III. Antibodies for the Detection of Alzheimer's Disease

A. Useful antigens

Useful antigens for the production of antibodies which recognize the 33 kD protein include the 33 kD protein; the C2 fragment of APP (amino acids 644–676 (SEQ ID NO:5); naturally occurring annexin V or fragments thereof; recombinant annexin V or fragments thereof; synthetic annexin V or fragments or homologs thereof; and recombinant or synthetic C2 fragments of APP. In addition, protein or peptide antigens which, regardless of their origin, length, or degree of exact homology with naturally occurring annexin V or C2 fragment of APP, lead to the production of antibodies which bind specifically to the 33 kD protein, may be useful in the methods of the invention. The crystal structure of rat annexin V has been determined (Concha et al., Science 261:1321, 1993), thus, facilitating the selection of annexin V peptides which are useful as antigens. The useful antigens described above may be used to generate either polyclonal or monoclonal antibodies. For example, the C2 fragment of APP may be used as an antigen to generate antibodies which are diagnostic for AD is described below in Example I.

The EMBL/GenBank accession numbers for annexin V and APP are J03899 and Y00264, respectively. The availability of these sequences allows the manufacture of additional immunogenic peptides using commonplace techniques of molecular biology.

B. Methods for generating antibodies Monoclonal antibodies

The hybrid cell lines of the invention may be produced by various methods generally known to those of ordinary skill in the art (Harlow et al., Antibodies, A Laboratory Manual, Cold Spring Harbor Laboratory Press, Cold Spring Harbor, N.Y.). In general, the method involves immunizing suitable mammals (such as mice) with the antigens of interest, fusing antibody producing cells isolated from the spleen of the animal with myeloma cells, cloning the resulting hybrid cells, and selecting those cells which produce the desired monoclonal antibody which binds the antigen of interest.

Immunizations are usually performed with purified antigens. The usual mammals used for immunizations are mice, especially CD-1 mice, but other mammals and mouse strains may also be employed. The immunizations are performed in a manner known in the art, such as by administering intraperitoneally, intravenously and/or subcutaneously three to six injections each containing an appropriate amount of purified antigen (i.e., from about 1 mg to about 50 mg) at intervals of about one to six weeks, usually together with an adjuvant that stimulates the production of lymphocytes, e.g., complete or incomplete Freund's adjuvant.

Antibody producing cells present in the spleen of the immunized animals are taken from the animal two to six days after the last ("booster") immunization and fused with myeloma cells of a suitable cell line. Myeloma cell lines and cell lines derived therefrom are known as suitable fusion partners. The myeloma cell line is generally derived from the same species as the immunized mammal, since intra-species hybrids are more viable than inter-species hybrids.

Myeloma cells that lack the enzyme hypoxanthine-guaninephosphoribosyl transferase (HGPRT) or the enzyme thymidine kinase (TK) and which do not survive in a selective culture medium containing hypoxanthine, aminopterin and thymidine (HAT medium), can be employed. Myeloma cells and cell lines prepared therefrom that do not survive in HAT medium and do not secrete any immunoglobulins or parts thereof, for example, the cell line XS63, can also be used (XS63 cells are available from the American Type Culture Collection, Rockville, Md., ATCC# TIB 17). Various fusion-promoters, for example, Sendai virus or other paramyxoviruses, optionally in UV-inactivated form, calcium ions, surface-active lipids, such as isolecithin, or polyethylene glycol ("PEG") may also be employed. Myeloma cells are usually fused with a three-to twenty-fold excess of spleen cells from immunized animals in a solution containing from about 30 to 50% PEG having a molecular weight of about 1000 to 4000 daltons. Exposure to PEG for about 2 to 3 minutes appears to be optimal to prevent toxicity to the cells; temperatures of about 37° C., are recommended. After fusion the cells are partitioned out and cultured in selective HAT medium.

Suitable culture media for the growth of the hybrid cells are customary standard culture media, for example, RPMI Medium or medium containing 20% fetal calf serum which is supplemented with antibiotics. At the beginning of cell growth, so-called feeder cells (e.g., normal mouse peritoneal exudate cells, spleen cells, bone marrow macrophages or the like) can be added. At regular intervals, the culture media may be supplemented by selective HAT medium to prevent hybrid cells from being overgrown by ordinary myeloma cells.

The cell culture supernatants of the hybrid cells surviving HAT selection are examined for the presence of the desired monoclonal antibodies. Advantageously, the cell supernatants are tested in an immunoassay, for example, enzyme immunoassay, that demonstrates the binding of monoclonal antibodies to the antigen of interest.

Those hybridomas which produce antibodies having the desired specificity as well as other desirable characteristics such as thermostability can then be maintained as viable cultures and/or frozen for storage.

Large quantities of the desired monoclonal antibodies can also be obtained by multiplying the hybridoma cells in vivo. For this purpose, antibody producing hybridomas are inoculated intraperitoneally into syngenic mammals, and after 1 to 3 weeks, the antibodies are isolated from ascites fluid of those mammals. For example, hybrid cells originating from CD-1 mice can be injected intraperitoneally into CD-1 mice that have previously been pretreated intraperitoneally with a hydrocarbon such as 2, 6, 10, 14-tetramethylpentadecane (pristane) to prevent fluid drainage from the intraperitoneal cavity, and after 8 to 10 days, ascites fluid is taken from these animals.

The present invention encompasses all monoclonal antibodies exhibiting the characteristics of the antibodies described herein. In other words, antibodies having the patterns of reactivity illustrated herein are within the scope of the invention regardless of the immunoglobulin class or subclass to which they belong. For example, a monoclonal antibody exhibiting the characteristics described herein may be of class IgG1, IgGa, IgGb, IgG3, or of classes IgM, IgA, or of other known Ig classes. Furthermore, while a hybrid cell line generated from a known mouse myeloma and spleen cells from a known species of immunized mouse cannot be further identified except by reference to the antibody produced by that specific hybrid cell line, all hybrid cell lines producing antibodies having the reactivity characteristics described above are within the present invention.

Polyclonal antibodies

The polyclonal antibodies of the invention may be produced by various methods generally known to those of ordinary skill in the art (Sambrook et al., Molecular Cloning, A Laboratory Manual, 2nd edn., Cold Spring Harbor Laboratory Press, Cold Spring Harbor, N.Y.; Harlow et al., Antibodies, A Laboratory Manual, Cold Spring Harbor Laboratory Press, Cold Spring Harbor, N.Y.). In general, the methods involve immunizing suitable mammals with the antigen of interest, bleeding the mammals, and preparation of antiserum from the mammal's blood. Immunizations are usually performed with purified antigens. The usual mammals used for immunizations are rabbits, but other mammals including goats and mice may also be employed. Antigens are injected via popliteal lymph nodes, intradermally, subcutaneously, or into a single intramuscular site.

Although the immunization schedule will vary according to the nature of the antigen, the amount of antigen available, the immunogenicity of the antigen, and the mammal used, a reasonable schedule for a rabbit is as follows. One hundred $\mu$g of antigen is dissolved in 0.5 ml of a buffer in which the antigen is soluble, and the solution is emulsified with an equal volume of Freund's complete adjuvant. One-half ml of emulsified antigen-adjuvant is injected into each of two limbs of the animal and 4–6 weeks later, 0.25 ml of the emulsified antigen-adjuvant is injected into another limb. Twenty-40 ml of blood should be drawn 7–10 days after each booster injection, serum prepared, and tested for the presence of the antibody by standard methods (ELISA, Western, RIA, or immunoprecipitation). Animals that have responded can be boosted at regular intervals until a high titer of antibody is attained. Blood (40 ml) then can be withdrawn weekly until the titer drops.

In order to prepare the antiserum, blood is collected from animals that have been fasted for several hours and then allowed to clot at room temperature. A glass rod or sealed pasteur pipet is then used to "ring" the clot. During the next several hours the clot will retract to about half its original volume, leaving the antiserum as a straw-colored liquid. The antiserum is then transferred to a fresh tube and the clot centrifuged at 1500 g for 10 minutes at room temperature. The supernatant is combined with the previously removed antiserum, the clot discarded, and the antiserum stored as either a lyophilized powder, at −20° C., −70° C. or at 4° C. in the presence of 0.02% sodium azide.

Both the monoclonal and polyclonal antibodies produced in vitro or in vivo may be purified using various methods, for example, affinity chromatography, gel filtration chromatography, ion-exchange chromatography or DEAE-cellulose chromatography. Optionally, selected proteins in the culture supernatants or ascites fluid, including the desired antibodies, may be precipitated using specific concentrations of ammonium sulphate or the like before being subjected to chromatography.

C. Methods for screening for antibodies useful for diagnosing AD.

Screening for useful antibodies can be achieved by the use of immunoassays. The immunoassay method of the present invention is preferably based on modified enzyme immunoassays, e.g., inhibition ELISA, Western blots, immunoprecipitation, slot or dot blot assays.

Depending upon the particular protocol employed, unlabeled or enzyme-labeled derivatives of antibodies are used. In the case where specific antibodies are not enzyme-labeled, a different detectable marker, for example, an enzyme-labeled antibody capable of binding to the first antibody, may be employed. Highly purified p33 can be used as a standard to calculate unknown concentrations of p33 in a sample. The sample to be quantified is either bound to solid phase or reacts with immobilized antibodies or is preincubated with specific antibodies to form and antigen-antibody complex.

To demonstrate how an immunoassay of this invention can be performed, the inhibition ELISA is described in detail below. First, the purified p33 is immobilized on a solid support. Any of the common supports used in immunoassays may be employed. Suitable solid supports include, for example, the inner walls of glass tubes and polystyrene based microtiter plates, or solid particles made from various materials such as polypropylene, polystyrene, polyethylene, and glass. After preincubation of the sample with the primary antibody, free primary antibody not complexed with the antigen present in the sample solution binds to the immobilized protein. Any substances in the sample which do not bind during this step are washed from the solid support. The solid support is then contacted with an enzyme-labeled secondary antibody which is capable of binding to the primary antibody which is bound to the immobilized antigen. After separation of any unbound enzyme-labeled secondary antibody from the solid support, the complex is incubated with an enzyme substrate capable of reacting with the enzyme of the enzyme-labeled secondary antibody to produce a detectable reaction product. The product of the enzymatic reaction is then measured and correlated with values of a standard curve of known concentration of antigen. The amount of p33 in the sample is calculated from the standard curve.

The immunoassay methods of the present invention can also employ, dependent upon the particular protocol, unlabeled or radioactively labeled derivatives of antibodies which bind p33, either alone or in combination. Any of the known modifications of the radioimmunoassay ("RIA"), for example, homogeneous RIA, heterogeneous RIA, competitive RIA, and sandwich RIA may be employed.

The immunoassay method of the present invention may also be other known immunoassay methods, for example, fluorescent immunoassays using antibody conjugates or antigen conjugates of fluorescent substances such as fluorescein or rhodamine, Ouchterlony double diffusion analysis, and immunoassays employing an avidin-biotin or streptavidin-biotin detection systems.

The antibodies may be bound to other solid matter such as glass beads with and without coating, or sepharose, sephadex, or acrylic beads. Antigen bound to these antibodies may be detected on the beads or after elution on membranes (slot blot) or ELISA-plates (inhibition ELISA).

D. Use of Antibodies for diagnosing AD.

Antibodies found to be useful in the immunoassays described above can be used to diagnose AD in symptomatic patients. Any of the immunoassays described above can be used to analyze lumbar cerebral spinal fluid (CSF) obtained from patients by standard methods (The Merck Manual 12th edn., D. N. Holvey, Ed., Merck Sharp and Dohne Research Labs Publishing, New Jersey, 1972. pp. 1746–1748).

The useful antibodies described above can also be used for postmortem diagnosis of AD. The immunoassays listed above can be used for analysis of ventricular CSF (Appleyard et al., Brain 110:1309, 1987; Wester et. al., Journal of Neurochemistry 54:1148, 1990) and brain homogenates (Takeuchi et al., J. Neurochemistry 58:1526 1992). In addition, immunostaining of sectioned brain tissue can be carried out (Immunohistochemistry, A. C. Cuello, Ed., John Wiley and Sons, New York, 1983, p. 501).

The above described assays can be facilitated by the use of kits which contain the reagents required for carrying out the assays. The different antibodies that can be used in the assays will have different total binding levels in different assays. Thus, the levels of antibody binding to samples from AD patients should be compared to levels of antibody binding to samples from control patients. An increase of 150 percent in AD samples compared to control samples is considered diagnostic for AD.

IV. Identification of Compounds that Decrease the Level of p33

We have shown that p33 is specifically enriched in CSF and brain homogenates from Alzheimer's patients relative to controls. Thus, administering compounds which decrease levels of p33 is useful for treating Alzheimer's disease.

Screening of compounds for the ability to decrease p33 levels is carried out as follows. First, compounds are tested in cultured cells. Second, compounds which test positive in the cultured cells are tested in an animal model system.

In the cell culture assay, cells that express p33 (e.g., PC12 cells transfected with A4-C, see Example I, below, for method; or, a fibroblast sample from a patient. Fibroblasts may be obtained from individuals according to the procedure of Willers et al., Pathobiology 59:357, 1991, herein incorporated by reference. See also Ham et al., In Vitro 14:11, 1978 who teach methods for growing fibroblasts in cell culture. About 0.05 to about 0.1 g of fibroblasts is needed to carry out the analysis), are cultured in the presence of the candidate compound. The level of p33 in the cells can be determined by the methods described below (see Example I).

Compounds found to decrease p33 levels in the cell culture assay are further tested in animal model systems. A candidate compound is administered to an animal which expresses p33. The effect of the compound on the level of p33 is determined by Western analysis (see Example I, below) of mouse brain homogenates. Whole brains are dissected from mice killed by cervical dislocation. Homogenate preparation is carried out as described below for human brain homogenate preparation (Example II, below; see also Takeuchi et al., Journal of Neurochemistry 58:1526. 1992). Immunostaining of thin sections prepared from the mouse brain can also be performed to determine the levels p33 (Immunohistochemistry, A. C. Cuello, Ed., John Wiley and Sons, New York, 1983, p. 501).

V. Use of Compounds in the Treatment of Alzheimer's Disease.

The invention provides methods for identifying compounds which decrease the level of p33. Thus, the compounds identified by this method can be used to treat patients. The compounds can be administered to the patient by any appropriate method suitable for the particular compound, e.g., orally, intravenously, parentally, transdermally, or transmucosally. Therapeutic doses are determined specifically for each compound, most administered within the range of 0.001–100.0 mg/kg body weight, or within a range that is clinically determined as appropriate by those skilled in the art.

The following examples are meant to illustrate, but not limit, the methods and compositions of the present invention. Other suitable modifications and adaptations of the variety of conditions and parameters normally encountered in immunodiagnostics which are obvious to those skilled in the art are within the spirit and scope of the present invention.

EXAMPLES

Example 1

Isolation and characterization of TC2 antibody

Peptide C2 of APP (amino acids 644–676 (SEQ ID NO:5) was synthesized by a Peptide synthesizer 430A (Applied Biosystems) and purified by reversed phase HPLC. The synthetic C2 peptide was coupled to keyhole limpet hemocyanine (KLH) with glutaraldehyde, and used for immunization. The antibodies were affinity-purified on a peptide coupled column after being purified as IgG (McKinney et al., J. Immunology 96:271, 1987).

The TC2 antibody was characterized by Western blot analysis. TC2 detected the 33 kD protein in lysates prepared from PC12 cells transfected with A4-C (FIGS. 3, 4, 5, 6, 7, and 10), brain homogenates of mice transgenic for A4-C (FIG. 4), purified p33 (FIGS. 7 and 10), and purified annexin V (FIG. 10). Preparation and Western blot analysis of PC12 cell lysates is described below.

Cell culture and transfection

PC12 cells were cultured on polystyrene culture dishes coated with rat tail collagen in DMEM supplemented with 5% normal horse serum, 5% fetal bovine serum (FBS) and 0.1 mg/ml gentamicin. Cell cultures were maintained at 37° C. in a humidified atmosphere containing 10% $CO_2$. PC12 cells were differentiated with 50 ng/ml NGF (Boehringer Mannheim) in DMEM containing 1% FBS and ITS (insulin transferrin-sodium selenite medium supplement, Sigma). PC12 cells overexpressing A4-C were generated as described previously (Marotta et al., Proc. Natl. Acad. Sci. USA 86:337, 1989).

Cell lysate preparation

One plate (100 mm) of the transfected cell culture was harvested and washed three times with TBS. Lysis buffer (20 mM Tris-HCl (pH 8.0) containing 150 mM NaCl, 1% (w/v) Triton X-100, 1 mM EDTA, 1 mM EGTA, 1 mM PMSF, 1 mM Benzamidine, 2 μg/ml leupeptin and 2 μg/M pepstatin) was added to the cell pellet and incubated at 4° C. following 20 second sonication. Supernatant was subjected to Western blot analysis.

Gel electrophoresis

Samples for Western blot analysis were pre-treated with 2% sodium dodecyl sulfate (SDS) and 5% 2-mercaptoethanol (2-ME) for 5 minutes at 95° C. and then fractionated by Laemmli SDS-PAGE (Schägger et al., Analytical Biochemistry 166:369, 1987).

Western blot analysis

Electroblotting was performed according to Towbin et al. (Proc Natl Acad Sci USA 76:4350, 1979) in a transfer buffer containing 15% methanol, 25 mM Tris, and 192 mM glycine, pH 8.3. Proteins were transferred electrophoretically onto polyvinylidene difluoride membrane (Immobilon-P, Millipore Corp., Bedford, Mass. U.S.A) by applying 1 A of constant current for 2 hours at 4° C. The blot was incubated with 5% nonfat dry milk solution containing 2 mM EGTA, 0.15 M NaCl in 50 mM Tris-Hcl, pH 7.4 (blocking buffer), for 1 hour at room temperature. The blot was incubated with TC2 antisera (1:7,500) overnight at 4° C., followed by a incubation with alkaline phosphatase-conjugated goat anti-rabbit immunoglobulin G (Promega) for 5 hours at 4° C. After several washes of the blots with 50 mM Tris-Hcl, pH 7.5, 0.15M NaCl, alkaline phosphatase was visualized by standard methods (Harlow et al., Antibodies, A Laboratory Manual, Cold Spring Harbor Laboratory Press, Cold Spring Harbor, N.Y.).

Example II

TC2 antibody detects the 33 kD diagnostic band in brain homogenates from AD affected patients Postmortem human brains were obtained from the McLean Hospital Brain Tissue Resource Center (Belmont, Mass. U.S.A.; Dr. Edward Bird, director). Ten control brains (mean age ±S.E.M.=69.4±3.7) and five AD brains from Alzheimer's disease individuals (72.2±2.7) were used. Tissues were homogenized immediately after dissection in 10 volumes of cold 20 mM Tris-HCl, pH 7.4, containing 0.32M sucrose, 2 mM EDTA, 2mM DTT, 1 mM phenylmethylsulphonyl fluoride, and 1 mM benzamidine (0.32M sucrose buffer). The homogenate was centrifuged at 15,000 g for 30 minutes at 4° C. The supernatant fraction (soluble fraction) was collected and assayed by Western blot analysis (FIG. 11A). The pellets were resuspended in 0.32M sucrose buffer and centrifuged at 15,000 g for 30 minutes at 4° C. Supernatants were discarded, and the pellets (membrane fraction) were then assayed by Western blot analysis (FIG. 11A). Western analysis of the soluble and membrane fractions with TC2 antibody revealed the presence of 33 kD protein in human brain and showed that in AD brains, the 33 kD protein increased both in soluble fractions (18.9%, $p<0.05$) and membrane fractions (97.7%, $p<0.01$), relative to the control brains (FIG. 11B).

Example III

TC2 specifically detects the 33 kD protein in Ventricular CSF of AD patients

Ventricular CSF was obtained from AD (Patient #: B1338) and control (Patient #: 1533) Patients by standard methods (The Merck Manual 12th ED. D. N. Holvey, Ed., Merck Sharp and Dohme Res. Labs Publishing, New Jersey, 1972, pp 1746–1748). Postmortem thin sectioning of patient B1338 showed senile plaques and neurofibrillary tangles of the anterior frontal cortex, posterior frontal cortex, parietal cortex, occipital cortex, hippocampus, caudate, putamen, accumbens, and amygdala, and senile plaques and protoplaques of the putamen and globus pallidus. The ventricular CSF from the AD and control patients was concentrated 10-fold to protein concentrations of 2.8 mg/ml and 1.04 mg/ml, respectively (protein concentrations were determined by the method of Bradford, Analytical Biochemistry 72:248, 1976). 70 µl of each sample were fractionated by SDS-PAGE (Laemmli, Nature 227:680, 1970) on a 4–12% gradient gel. Western blot analysis was carried out as described in Example I (FIG. 12). The level of 33 kD protein detected by TC2 in AD CSF was 300 percent more than in control CSF.

Example IV

Annexin V antibody (4431) specifically detects the 33 kD protein in Ventricular CSF from AD patients Analysis of Ventricular CSF with the Annexin antibody was carried out by the methods described in Example III, except that the blot was incubated with antibody 4431 instead of TC2 (FIG. 12). The level of 33 kD protein detected by antibody 4431 in AD CSF was 200 percent more than in control CSF.

Other Embodiments

The above specific examples are, therefore, to be construed as merely illustrative, and not limitative of the remainder of the disclosure in any way whatsoever.

From the above description, one skilled in the art can easily ascertain the essential characteristics of the present invention, and without departing from the spirit and scope thereof, can make various changes and modifications of the invention to adapt it to various usages and conditions. All publications cited herein are fully incorporated by reference herein in their entirety.

Other embodiments are in the following claims.

What is claimed is:

1. A method of detecting Alzheimer's disease in a human patient, said method comprising using an antibody that specifically recognizes Annexin V in an immunoassay to measure the amount of p33 present in a biological sample of said patient relative to the amount of p33 in a control sample from an unaffected human, a relative level of p33 in said sample from said patient 50 percent above the level of p33 in said control sample indicating a diagnosis of Alzheimer's disease in said patient, said immunoassay allowing a differentiation of protein mass.

2. The method of claim 1, wherein said biological sample is a lumbar CSF sample of said patient.

3. The method of claim 1, wherein said biological sample is a ventricular CSF sample of said patient.

4. The method of claim 1, wherein said biological sample is brain tissue homogenate of said patient.

5. The method of claim 1, wherein said immunoassay is Western blot analysis.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: Not Relevant
        ( D ) TOPOLOGY: Not Relevant ( i i ) MOLECULE TYPE: protein ( i x ) FEATURE:

( A ) NAME/KEY: Modified-site
( B ) LOCATION: 1
( D ) OTHER INFORMATION: /note= "Xaa at position 7 is unknown."

( x i ) SEQUENCE DESCRIPTION: SEQ ID NO:1:

| Asp | Lys | Val | Leu | Asn | Arg | Xaa | Glu | Phe | Val | Leu | Asn | Arg | Glu | Glu | Phe |
|---|---|---|---|---|---|---|---|---|---|---|---|---|---|---|---|
| 1 | | | | 5 | | | | | 10 | | | | | 15 | |

| Arg | His |
|---|---|

( 2 ) INFORMATION FOR SEQ ID NO:2:

( i ) SEQUENCE CHARACTERISTICS:
( A ) LENGTH: 319 amino acids
( B ) TYPE: amino acid
( C ) STRANDEDNESS: Not Relevant
( D ) TOPOLOGY: Not Relevant ( i i ) MOLECULE TYPE: protein ( x i ) SEQUENCE DESCRIPTION: SEQ ID NO:2:

| Met | Ala | Leu | Arg | Gly | Thr | Val | Thr | Asp | Phe | Ser | Gly | Phe | Asp | Gly | Arg |
|---|---|---|---|---|---|---|---|---|---|---|---|---|---|---|---|
| 1 | | | | 5 | | | | | 10 | | | | | 15 | |

| Ala | Asp | Ala | Glu | Val | Leu | Arg | Lys | Ala | Met | Lys | Gly | Leu | Gly | Thr | Asp |
| | | | 20 | | | | 25 | | | | | 30 | | | |

| Glu | Asp | Ser | Ile | Leu | Asn | Leu | Leu | Thr | Ala | Arg | Ser | Asn | Ala | Gln | Arg |
| | | 35 | | | | | 40 | | | | | 45 | | | |

| Gln | Gln | Ile | Ala | Gln | Glu | Phe | Lys | Thr | Leu | Phe | Gly | Arg | Asp | Leu | Val |
| | 50 | | | | | 55 | | | | | | 60 | | | |

| Asn | Asp | Met | Lys | Ser | Glu | Leu | Thr | Gly | Lys | Phe | Glu | Gly | Leu | Ile | Val |
| 65 | | | | | 70 | | | | | 75 | | | | | 80 |

| Ala | Leu | Met | Lys | Pro | Ser | Arg | Leu | Tyr | Asp | Ala | Tyr | Glu | Leu | Lys | His |
| | | | | 85 | | | | | 90 | | | | | 95 | |

| Ala | Leu | Lys | Gly | Ala | Gly | Thr | Asp | Glu | Lys | Val | Leu | Thr | Glu | Ile | Ile |
| | | | | 100 | | | | | 105 | | | | | 110 | |

| Ala | Ser | Arg | Thr | Pro | Glu | Glu | Leu | Arg | Ala | Ile | Lys | Gln | Ala | Tyr | Glu |
| | | | 115 | | | | | 120 | | | | | 125 | | |

| Glu | Glu | Tyr | Gly | Ser | Asn | Leu | Glu | Asp | Asp | Val | Val | Gly | Asp | Thr | Ser |
| | | 130 | | | | | 135 | | | | | 140 | | | |

| Gly | Tyr | Tyr | Gln | Arg | Met | Leu | Val | Val | Leu | Leu | Gln | Ala | Asn | Arg | Asp |
| 145 | | | | | 150 | | | | | 155 | | | | | 160 |

| Pro | Asp | Thr | Ala | Ile | Asp | Asp | Ala | Gln | Val | Glu | Leu | Asp | Ala | Gln | Ala |
| | | | | 165 | | | | | 170 | | | | | 175 | |

| Leu | Phe | Gln | Ala | Gly | Glu | Leu | Lys | Trp | Gly | Thr | Asp | Glu | Glu | Lys | Phe |
| | | | 180 | | | | | 185 | | | | | 190 | | |

| Ile | Thr | Ile | Leu | Gly | Thr | Arg | Ser | Val | Ser | His | Leu | Arg | Arg | Val | Phe |
| | | 195 | | | | | 200 | | | | | 205 | | | |

| Asp | Lys | Tyr | Met | Thr | Ile | Ser | Gly | Phe | Gln | Ile | Glu | Glu | Thr | Ile | Asp |
| | 210 | | | | | 215 | | | | | 220 | | | | |

| Arg | Glu | Thr | Ser | Gly | Asn | Leu | Glu | Asn | Leu | Leu | Leu | Ala | Val | Val | Lys |
| 225 | | | | | 230 | | | | | 235 | | | | | 240 |

| Ser | Ile | Arg | Ser | Ile | Pro | Ala | Tyr | Leu | Ala | Glu | Thr | Leu | Tyr | Tyr | Ala |
| | | | | 245 | | | | | 250 | | | | | 255 | |

| Met | Lys | Gly | Ala | Gly | Thr | Asp | Asp | His | Thr | Leu | Ile | Arg | Val | Ile | Val |
| | | | | 260 | | | | | 265 | | | | | 270 | |

| Ser | Arg | Ser | Glu | Ile | Asp | Leu | Phe | Asn | Ile | Arg | Lys | Glu | Phe | Arg | Lys |
| | | 275 | | | | | 280 | | | | | 285 | | | |

| Asn | Phe | Ala | Thr | Ser | Leu | Tyr | Ser | Met | Ile | Lys | Gly | Asp | Thr | Ser | Gly |

```
                        290                     295                         300
    Asp  Tyr  Lys  Lys  Ala  Leu  Leu  Leu  Leu  Cys  Gly  Gly  Glu  Asp  Asp
    305                      310                     315
```

(2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
    Val  Lys  Met  Asp  Ala  Glu  Phe  Arg  His  Asp  Ser  Gly  Phe  Glu  Gln  Met
    1                   5                        10                      15

Gln  Asn
```

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:4:

```
    Met  Asp  Lys  Val  Leu  Asn  Arg  Glu  Glu  Phe  Arg  His  Asp  Ser  Gly  Phe
    1                   5                        10                      15

Glu  Gln  Met  Gln  Asn
                    20
```

(2) INFORMATION FOR SEQ ID NO:5:

(i) SEQUENCE CHARACTERISTICS:
        (A) LENGTH: 33 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

```
    Thr  Leu  Val  Met  Leu  Lys  Lys  Lys  Gln  Tyr  Thr  Ser  Ile  His  His  Gly
    1                   5                        10                      15

Val  Val  Glu  Val  Asp  Ala  Ala  Val  Thr  Pro  Glu  Glu  Arg  His  Leu  Ser
                        20                       25                      30

Lys
```